United States Patent [19]

Acker et al.

[11] Patent Number: 4,608,078
[45] Date of Patent: Aug. 26, 1986

[54] BREFELDIN A DERIVATIVES AND THEIR USE FOR CONTROLLING UNDESIRABLE PLANT GROWTH

[75] Inventors: Rolf-Dieter Acker, Leimen; Rudolf Karl, Limburgerhof; Bruno Wuerzer, Otterstadt, all of Fed. Rep. of Germany

[73] Assignee: BASF Aktiengesellschaft, Ludwigshafen, Fed. Rep. of Germany

[21] Appl. No.: 560,965

[22] Filed: Dec. 13, 1983

[30] Foreign Application Priority Data

Dec. 22, 1982 [DE] Fed. Rep. of Germany ....... 3247379

[51] Int. Cl.⁴ .................. C07D 313/00; A01N 43/22
[52] U.S. Cl. ........................................ 71/88; 549/270; 549/214; 549/220
[58] Field of Search .............. 71/88; 549/270, 214, 549/220

[56] References Cited

U.S. PATENT DOCUMENTS 3,896,002  7/1975  Howard et al. ..................... 435/911

OTHER PUBLICATIONS

Corey et al., CA 85:77564z.
Yanagishita, CA 98:59899b.
Corey et al., CA 87:5431x, 87:5432y.
The Merck Index 10th Edition 1983, 1347, p. 189.
J. Fac. Agr. Kyushu Univ., 17 (1973), 129-136.
Reunion EUCAPPIA, Versailles, France, 1980, pp. 102-109.

Primary Examiner—Jane T. Fan
Attorney, Agent, or Firm—Keil & Weinkauf

[57] ABSTRACT

Brefeldin A derivatives of the formula

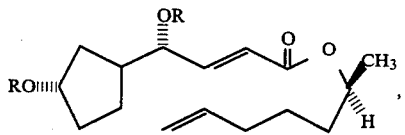

where R is alkyl, unsubstituted or substituted alkanoyl, unsubstituted or substituted aralkyl, unsubstituted or substituted benzoyl, a radical of the formula $(R^1O)_2P(O)-$ or a radical $R^2R^3R^4Si$, and the use of brefeldin A and brefeldin A derivatives of the formula I for combatting unwanted plant growth.

7 Claims, No Drawings

BREFELDIN A DERIVATIVES AND THEIR USE FOR CONTROLLING UNDESIRABLE PLANT GROWTH

The present invention relates to brefeldin A derivatives, herbicides which contain these compounds or brefeldin A as active ingredients and methods of controlling undesirable plant growth.

The literature discloses that brefeldin A has phytotoxic and fungitoxic properties (German Laid-Open Application DOS No. 2,325,330 and J.Fac.Agr. Kyushu Univ., 17 (1973), 129-136). However, this phytotoxic action is not a herbicidal action.

In Réunion EUCARPIA, Versailles, France, 1980, pages 102-109, it is stated that brefeldin A leads to lesions (symptoms of damage) at those points of the leaves which have first been penetrated by an injection needle and on which a defined volume of a solution of the substance has been applied. Obviously, it was intended to demonstrate the phytopathogenicity of the substance or of culture filtrates containing it.

We have found that brefeldin A derivatives of the formula

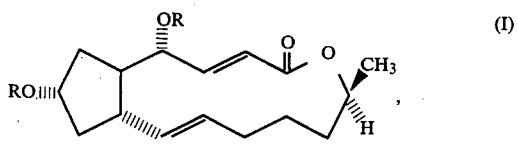

(I)

where R is $C_1$–$C_6$-alkyl, unsubstituted or halogen-substituted $C_2$–$C_7$-alkanoyl, aralkyl which is unsubstituted or substituted by halogen or $C_1$–$C_4$-alkyl, benzoyl which is unsubstituted or substituted by halogen or $C_1$–$C_4$-alkyl, a radical of the formula $(R^1O)_2P(O)$—, where $R^1$ is hydrogen or $C_1$–$C_4$-alkyl, or a radical $R^2R^3R^4Si$, where $R^2$, $R^3$ and $R^4$ are identical or different and are each $C_1$–$C_6$-alkyl, and brefeldin A and plant-tolerated salts of these compounds, have a herbicidal action and at the same time have a selective action on, and are tolerated by, certain crops.

In formula I, R can be $C_1$–$C_6$-alkyl, eg. methyl, ethyl or n-butyl, $C_2$–$C_7$-alkanoyl which is unsubstituted or substituted by halogen, such as chlorine, bromine or fluorine, eg. acetyl, propionyl, butyryl or trifluoroacetyl, $C_7$–$C_9$-aralkyl or benzoyl, each of which is unsubstituted or substituted by halogen, such as chlorine, or $C_1$–$C_4$-alkyl, such as methyl or ethyl, eg. benzyl, phenethyl, p-chlorobenzyl, m-chlorobenzyl or p-methylbenzyl, a radical of the formula $(R^1O)_2P(O)$—, where $R^1$ is hydrogen or $C_1$–$C_4$-alkyl, eg. $(HO)_2P(O)$—, $(CH_3O)_2P(O)$— or $(C_2H_5O)_2P(O)$—, or a radical of the formula $R^2R^3R^4Si$, where $R^2$, $R^3$ and $R^4$ are identical or different and are each $C_1$–$C_6$-alkyl, preferably $C_1$–$C_4$-alkyl, such as methyl, ethyl or n-butyl.

Brefeldin A derivatives of the formula I where R is $C_1$–$C_6$-alkyl, aralkyl which is unsubstituted or substituted by halogen or $C_1$–$C_4$-alkyl, or a radical of the formula $(R^1O)_2P(O)$— are obtained by reacting brefeldin A with a halide of the formula

R—X (II), where R has the above meanings and X is halogen, in the presence of an inert solvent and in the presence or absence of a base of from 20° to 100° C., preferably from 40° to 80° C.

Brefeldin A derivatives of the formula I where R is unsubstituted or halogen-substituted $C_2$–$C_7$-alkanoyl or benzoyl which is unsubstituted or substituted by halogen or by $C_1$–$C_4$-alkyl can be prepared by reacting brefeldin A with an anhydride of the formula $R^5$—CO—O—CO—$R^5$ (III), where $R^5$ is unsubstituted or halogen-substituted $C_1$–$C_6$-alkyl or is phenyl which is unsubstituted or substituted by halogen or by $C_1$–$C_4$-alkyl, in the presence of an inert solvent at from 80° to 120° C., or with an acid chloride of the formula $R^5$—CO—Cl (IV), where $R^5$ is unsubstituted or halogen-substituted $C_1$–$C_6$-alkyl or is phenyl which is unsubstituted or substituted by halogen or by $C_1$–$C_4$-alkyl, in the presence or absence of a base at from 20° to 120° C., preferably from 60° to 80° C.

The silylated brefeldin A derivatives in which R is a radical $R^2R^3R^4Si$ can be obtained by reacting brefeldin A with a chlorosilane of the formula

(V)

where $R^2$, $R^3$ and $R^4$ are each $C_1$–$C_6$-alkyl, in the presence of an inert solvent and of a base at from 20° to 70° C., or with a silyl derivative of acetamide, of trifluoroacetamide or of N-t-butylacetamide at from 0° to 50° C., preferably from 30° to 40° C.

Examples of suitable silyl derivatives of acetamide, of trifluoroacetamide and of N-t-butylacetamide are the trimethylsilyl, triethylsilyl and n-butyldimethylsilyl derivatives.

Examples of suitable solvents for the processes are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and beta, beta'-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic, cycloaliphatic and aromatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3- trimethylpentane, 2,3,3-trimethylpentane, octane, toluene, o-, m- and p-xylene and tetralin, esters, eg. ethyl acetate, ethyl acetoacetate and isobutyl acetate, amides, eg. formamide, methylformamide and dimethylformamide, ketones, eg. acetone and methyl ethyl ketone, alcohols, eg. methanol, ethanol and isopropanol, sulfoxides, eg. dimethyl sulfoxide, heteroaromatics, eg. pyridine, α-, β- and γ-picoline and pyrimidine, and mixtures of these. Advantageously, the solvent is used in an amount of from 100 to 2,000, preferably from 200 to 700, % by weight, based on starting material II or IV.

Suitable bases for the reaction of brefeldin A with a compound of the formula II, IV or V are tertiary amines, alkaline earth metal compounds, ammonium compounds and alkali metal compounds, as well as mixtures of these. Zinc compounds may also be used. Examples of such compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidine, N-ethylpyrrolidine, N-methylpiperidine, N-ethylpiperidine, N-methylpyrrolidone, N-ethylpyrrolidone, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, alpha-picoline, beta-picoline, gamma-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N'-dimethylcyclohexylamine, 2,6-lutidine, 2,4-lutidine, trifurylamine and triethylenediamine.

Apart from the above inorganic bases, other suitable compounds are, for example, sodium propionate, sodium butyrate, sodium isobutyrate, potassium formate, potassium acetate, potassium propionate, potassium butyrate, potassium isobutyrate, sodium methylate, sodium ethylate, sodium propylate, sodium isopropylate, sodium butylate, sodium isobutylate, sodium sec.-butylate, sodium tert.-butylate, sodium ethyleneglycolate, sodium propylene-1,2-glycolate, sodium propylene-1,3-glycolate, sodium diethyleneglycolate, sodium triethyleneglycolate, sodium dipropylene-1,2-glycolate, potassium methylate, potassium ethylate, potassium n-propylate, potassium isopropylate, potassium n-butylate, potassium isobutylate, potassium sec.-butylate, potassium tert.-butylate, potassium methyleneglycolate, potassium propylene-1,2-glycolate, potassium propylene-1,3-glycolate, potassium diethyleneglycolate, potassium triethyleneglycolate and potassium dipropylene-1,2-glycolate.

All of the processes can be carried out continuously or batchwise, under atmospheric or superatmospheric pressure; for the sake of simplicity, atmospheric pressure is preferred.

It is advantageous to use, for example, from 2.5 to 5 equivalents of the halide of the formula II, or 2.2 equivalents of the silyl derivative of acetamide, per equivalent of brefeldin A, or to employ a large excess of the anhydride of the formula III, since the anhydride can also serve as the solvent. The base is used in a 2-fold to 5-fold excess, based on brefeldin A.

Brefeldin A can be prepared by chemical synthesis, starting from D-mannitol and D-glutamic acid (Tetrahedron Lett. 32 (1979), 3021-3024).

EXAMPLE 1

2.0 parts of brefeldin A, 2.1 parts of N,O-bis-trimethylsilyltrifluoroacetamide and 8 parts of acetonitrile were combined, 0.3 part of trimethylchlorosilane was added, the reaction solution was stirred for 1 hour at room temperature and for 2 hours at 40° C. and was then evaporated down, and residual solvent was removed at 40° C. under 0.01 mbar. 2.4 parts of the bis-trimethylsilyl ether of brefeldin A were obtained as a viscous oil (active ingredient No. 1)

$^1$H-NMR in CDCl$_3$:
$\delta = 0.19$ (9H, (CH$_3$)$_3$Si)
$\delta = 0.12$ (9H, (CH$_3$)$_3$Si)

EXAMPLE 2

1.0 part of brefeldin A was dissolved in 10 parts of dry dimethylformamide, 3.7 parts of methyl iodide were added and 6.0 parts of silver oxide were then introduced a little at a time. After 1 hour at room temperature and 4 hours at 40°-50° C., the mixture was cooled, the residue was filtered off and the filtrate was stirred into water. It was then extracted with methylene chloride, and the methylene chloride phase was separated off, dried and evaporated down to give 8 parts of the dimethyl ether of brefeldin A (active ingredient No. 2)

$^1$H-NMR:
$\delta = 1.27$ (3H, OCH$_3$)
$\delta = 1.29$ (3H, OCH$_3$)

EXAMPLE 3

1 part of brefeldin A, 10 parts of acetic anhydride and 40 parts of glacial acetic acid were heated at 100° C. for 2 hours, after which the mixture was cooled, poured into 200 parts of ice-water and then filtered, and the residue was washed neutral. 1.2 parts of the bis-acetyl derivative of brefeldin A of melting point 121°-123° C. (active ingredient No. 3) were obtained.

For example, the following brefeldin A derivatives were obtained by a similar method:
  bis-(t-butyldimethylsilyl)ether of brefeldin A (active ingredient No. 4; viscous oil) and
  monosodium salt of brefeldin A (active ingredient No. 5; mp. >240° C.).

For example, the following brefeldin A derivatives of the formula I can be obtained by a similar method:

| Active ingredient No. | R | Mp. [°C.] |
| --- | --- | --- |
| 6 | F$_3$C—CO— | |
| 7 | (HO)$_2$P(O)— | |
| 8 | (CH$_3$O)$_2$P(O)— | |
| 9 | benzoyl | |
| 10 | 4-chlorobenzoyl | |
| 11 | propionyl | |

The brefeldin A derivatives of the formula I and brefeldin A may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, andureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I.

200 g/l bistrimethylsilyl ether of brefeldin A
50 g/l calcium dodecylbenzene sulfonate
50 g/l ethoxylated castor oil make-up to 1,000 ml xylene

II.

150 g/l bisacetyl derivative of brefeldin A
50 g/l calcium dodecylbenzene sulfonate
50 g/l alkoxylated isooctylphenol
150 g/l ethoxylated isooctylphenol make-up to 1,000 ml cyclohexanone

III.

150 g/l bisacetyl derivative of brefeldin A
50 g/l calcium dodecylbenzene sulfonate
50 g/l alkoxylated isooctylphenol make-up to 1,000 ml cyclohexanone.

The active ingredients, or agents containing them, may be applied pre- or postemergence. Preferably, the brefeldin A derivatives, or agents containing them, are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and their growth stage, and varies from 0.05 to 6 kg/ha and more, but is preferably from 0.5 to 4.0 kg/ha.

The influence of brefeldin A derivatives of the formula I and of brefeldin A on the growth of unwanted and crop plants is demonstrated in greenhouse experiments.

I. The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown.

For the postemergence treatment, the plants were first grown in the vessels to a height of from 3 to 15 cm, depending on growth form, before being treated.

The compounds were emulsified in water as vehicle, and sprayed through finely distributing nozzles. The application rate was 2.0 kg of active ingredient per hectare.

The test plants were *Triticum aestivum* and Ipomoea spp. The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

On postemergence application, for example active ingredient no. 1, applied at a rate of 2.0 kg/ha, combated for instance broadleaved weeds and was selective in winter wheat.

II. The vessels employed were flats of ®Styropor (27 cm long, 18 cm wide and 5 cm high). The test plants Amaranthus spp., *Euphorbia heterophylla*, Ipomoea spp., *Triticum aestivum* and Zea mays were sown in rows next to each other. The substrate was a peat-enriched potting soil. Bearing the heat-loving species in mind, the flats were set up in the 20° to 35° C. range in the greenhouse.

For the postemergence treatment, the plants were allowed to grow to a height of from 3 to 18 cm, depending on growth form, before being treated. The active ingredient was then emulsified in water as vehicle and sprayed through finely distributing nozzles. The amount applied was, for example, 4.0 kg/ha. The plants were tended, and the action was assessed, as under I.

In this postemergence treatment, for instance active ingredient no. 3 combatted unwanted broadleaved plants, Indian corn and wheat not being damaged, or at most very slightly and temporarily.

We claim:

1. A brefeldin A derivative of the formula

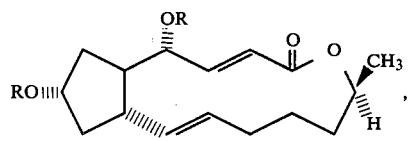

where R is $C_1$–$C_6$-alkyl, $C_7$–$C_9$-aralkyl which is unsubstituted or substituted by halogen or $C_1$–$C_4$-alkyl, benzoyl which is unsubstituted or substituted by halogen or $C_1$–$C_4$-alkyl, a radical of the formula $(R^1O)_2P(O)$—, where $R^1$ is hydrogen or $C_1$–$C_4$-alkyl, or a radical $R^2R^3R^4Si$, where $R^2$, $R^3$ and $R^4$ are identical or different and are each $C_1$–$C_6$-alkyl.

2. A brefeldin A derivative of the formula I as claimed in claim 1, where R is a radical $R^2R^3R^4Si$.

3. A brefeldin A derivative of the formula I as defined in claim 1, wherein R is $Si(CH_3)_3$.

4. A herbicidal composition containing inert additives and a herbicidally effective amount of a brefeldin A derivative of the formula

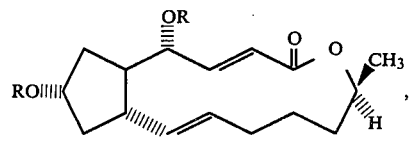

where R is $C_1$–$C_6$-alkyl, $C_7$–$C_9$-aralkyl which is unsubstituted or substituted by halogen or $C_1$–$C_4$-alkyl, benzoyl which is unsubstituted or substituted by halogen or $C_1$–$C_4$-alkyl, a radical of the formula $(R^1O)_2P(O)$—, wherein $R^1$ is hydrogen or $C_1$–$C_4$-alkyl, or a radical $R^2R^3R^4Si$, where $R^2$, $R^3$ and $R^4$ are identical or different and are each $C_1$–$C_6$-alkyl.

5. A herbicidal composition as claimed in claim 1, containing from 0.1 to 95 wt% of brefeldin A derivative of the formula I.

6. A method of combatting the growth of unwanted broadleaved plants that are growing among Indian corn or wheat, wherein the plants and/or the area to be kept free from unwanted plant growth are treated with a herbicidally effective amount of brefeldin A or a brefeldin A derivative of the formula

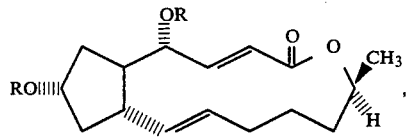

where R is $C_1$–$C_6$-alkyl, unsubstituted or halogen-substituted $C_2$–$C_7$-alkanoyl, $C_7$–$C_9$-aralkyl which is unsubstituted or substituted by halogen or $C_1$–$C_4$-alkyl, benzoyl which is unsubstituted or substituted by halogen or $C_1$–$C_4$-alkyl, a radical of the formula $(R^1O)_2P(O)$—, where $R^1$ is hydrogen or $C_1$–$C_4$-alkyl, or a radical $R^2R^3R^4Si$, where $R^2$, $R^3$ and $R^4$ are identical or different and are each $C_1$–$C_6$-alkyl.

7. A method of combatting the growth of unwanted broadleaved plants, wherein the plants and/or the area to be kept free from unwanted plant growth are treated with a herbicidally effective amount of a brefeldin A derivative of the formula

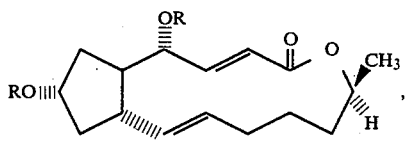

where R is $C_1$–$C_6$-alkyl, unsubstituted or halogen-substituted $C_2$–$C_7$-alkanoyl, $C_7$–$C_9$-aralkyl which is unsubstituted or substituted by halogen or $C_1$–$C_4$-alkyl, benzoyl which is unsubstituted or substituted by halogen or $C_1$–$C_4$-alkyl, a radical of the formula $(R^1O)_2P(O)$—, where $R^1$ is hydrogen or $C_1$–$C_4$-alkyl, or a radical $R^2R^3R^4Si$, where $R^2$, $R^3$ and $R^4$ are identical or different and are each $C_1$–$C_6$-alkyl.

* * * * *

UNITED STATES PATENT AND TRADEMARK OFFICE
CERTIFICATE OF CORRECTION

PATENT NO. : 4,608,078
DATED     : August 26, 1986
INVENTOR(S) : ACKER et al.

It is certified that error appears in the above-identified patent and that said Letters Patent is hereby corrected as shown below:

In the Abstract: please add missing bond:

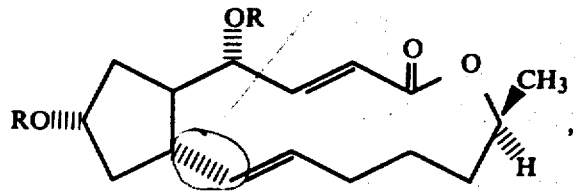

Signed and Sealed this

Eighteenth Day of November, 1986

*Attest:*

DONALD J. QUIGG

*Attesting Officer*   *Commissioner of Patents and Trademarks*